United States Patent [19]
Cohen et al.

[11] Patent Number: 5,755,809
[45] Date of Patent: May 26, 1998

[54] FEMORAL HEAD CORE CHANNEL FILLING PROTHESIS

[75] Inventors: Robert C. Cohen, Rockaway Twsp., N.J.; Michael J. Christie, Nashville, Tenn.

[73] Assignee: Implex Corporation, Allendale, N.J.

[21] Appl. No.: 717,204

[22] Filed: Sep. 20, 1996

Related U.S. Application Data

[63] Continuation of Ser. No. 476,019, Jun. 7, 1995, abandoned.

[51] Int. Cl.⁶ .................. A61F 2/36; A61B 17/74
[52] U.S. Cl. .................. 623/23; 606/65
[58] Field of Search .................. 606/76, 65, 67, 606/72, 62; 623/18, 23; 433/173

[56] References Cited

U.S. PATENT DOCUMENTS

| | | | |
|---|---|---|---|
| 3,852,045 | 12/1974 | Wheeler et al. | 606/76 X |
| 4,259,072 | 3/1981 | Hirabayashi et al. | 433/173 |
| 5,135,394 | 8/1992 | Hakamatsuka et al. | 433/173 |
| 5,282,861 | 2/1994 | Kaplan | 623/16 |
| 5,375,956 | 12/1994 | Pennig | 411/389 |
| 5,443,515 | 8/1995 | Cohen et al. | 623/17 |

FOREIGN PATENT DOCUMENTS

| | | | |
|---|---|---|---|
| 2910627 | 9/1980 | Germany | 623/18 |
| 3305874 | 12/1988 | Japan | 606/76 |

*Primary Examiner*—David H. Willse
*Attorney, Agent, or Firm*—Plevy & Associates

[57] ABSTRACT

A prosthesis for interfacing with an internal region of a bone of a given structure and function such as a femoral head and/or neck, wherein the internal region of the bone can be an avascular necrotic region. The prosthesis comprises porous filling member for filling a cored channel provided in the internal region of the bone to provide mechanical stability which preserves the function and the structure of the bone and accommodate an ingrowth of healthy vascularized bone tissue into the internal region of the bone. Also, a method for mechanically stabilizing a bone using the prosthesis.

9 Claims, 2 Drawing Sheets

FEMORAL HEAD CORE CHANNEL FILLING PROTHESIS

This is a continuation of application Ser. No. 08/476,019, filed on Jun. 7, 1995, entitled FEMORAL HEAD CORE CHANNEL FILLING PROTHESIS, now abandoned.

FIELD OF INVENTION

This invention relates generally to a bone prosthesis and more particularly, to a bone prosthesis used in the treatment of avascular necrosis of the femoral head.

BACKGROUND OF THE INVENTION

Up to 20,000 people in the United States develop avascular necrosis of the femoral head each year. Avascular necrosis of the femoral head develops when the blood supply to the femoral head is interrupted. The interruption can be the result of many factors, some of which are unknown, however, whatever the cause, the disease is degenerative. Thus, over a period of time, the rate of viable bone resorption in the secondary degenerative stages of the disease will lead to femoral head and/or neck collapse and fracture. When this occurs, hip reconstructive surgery becomes necessary.

Accordingly, it is desirable to delay or avoid the need for total hip replacement surgery by performing other less radical surgical procedures that are available today. It is generally agreed that the recommended time for performing these less radical surgical procedures is in the early stages of the disease. In the early stages of avascular necrosis, the femoral head has not structurally failed and typically displays no signs of any radiographic crescent images or subchondral lucency. In particular, the pathological process in the early stages of the disease, is confined to a wedge-shaped area of necrosis in the superior weight-bearing portion of the femoral head. This area is subject to collapse and fracture at the junction of the living and dead bone at the level of the "creeping substitution."

A common surgical procedure that is presently used prior to collapse and fracture of the femoral head and/or neck in an effort to delay or avoid hip reconstructive surgery, is core decompression. This procedure is generally implemented to preserve the function and the structure of the femoral head and/or neck and to relieve the debilitating pain associated with the disease.

Core decompression involves repairing the necrotic area by coring and, optionally, filling the cored area with a bone graft. More specifically, core decompression involves a technique wherein through a lateral trochanteric approach, an 8 to 10 mm cylindrical core of bone is removed from the anterolateral segment of the femoral head which creates an open cylindrical channel therein. The open channel operates to relieve pressure and provides a conduit for biological functions which assist in repairing the bone. Optionally, the open channel in the femoral head can be filled with either a vascularized or a non-vascularized bone graft. Vascularized bone grafts are used in an attempt to assist in the ingrowth of vascular cellular tissue into the necrotic area to enhance revascularization thereof in order to arrest the progression of the necrosis. Non-vascularized "cortical" bone grafts are used in an attempt to provide some structural stability to the femoral head and/or neck during the healing process. Unfortunately, due to the existence of problems associated with inaccurate matching of the open channel and the quality of these bone grafts, collapse of the necrotic area still often occurs.

In an attempt to provide additional structural stability to the femoral head and/or neck, the prior art has provided solid metal drills or threaded pins which are implanted in the femoral head. However, due to the relative minor diameter of these drills and pins and their inherent lack of any biological interface characteristics, collapse and fracture of the femoral head and/or neck still-commonly occurs.

Furthermore, major complications are associated with core decompression. For example, collapse of the femoral wedge-shaped area of necrosis occurs from the lack of bony structural support and the continuing degenerative changes caused by the disease.

Thus, the objective of preserving the function and structure of the femoral head and/or neck by performing a core decompression and filling the open channel with a bone graft remains unfulfilled.

It is, therefore, a primary object of the present invention to provide a bone core channel filling prosthesis which mechanically stabilizes the femoral head and/or neck.

It is a further object of the present invention to provide a bone core channel filling prosthesis which enables the ingrowth of vascular cellular tissue into a necrotic region of the bone to enhance revascularization and slow the progression of the necrosis.

SUMMARY OF THE INVENTION

A prosthesis for interfacing with an internal region of a bone of a given structure and function such as a femoral head and/or neck, wherein the internal region of the bone can be an avascular necrotic region. The prosthesis comprises porous filling means for filling a cored channel provided in the bone, whereby the porous filling means provides mechanical stability which preserves the function and the structure of the bone while also accommodating an ingrowth of healthy vascularized bone tissue into the internal bone region in instances where the internal bone region is an avascular necrotic region of the bone.

The present invention also describes a method for mechanically stabilizing a femoral head to substantially prevent the femoral head from collapsing and fracturing. The method comprises removing a core of bone from an anterolateral segment of the femoral head to provide an open channel therein. Next, the open channel is filled by inserting the filling prosthesis of the present invention.

BRIEF DESCRIPTION OF THE DRAWINGS

The novel features of the present invention will become apparent from the following detailed description of the invention illustrated in the accompanying drawings, wherein.

DETAILED DESCRIPTION OF THE INVENTION

The present invention relates to a bone core channel filling prosthesis and method for implanting same. Although the present invention is especially suited for use in core channels created by a core decompression of the femoral head, persons of ordinary skill in the art will recognized that the present invention can be used as a bone core channel filling prosthesis in any other type of bone or clinical indication.

Figure 1A:
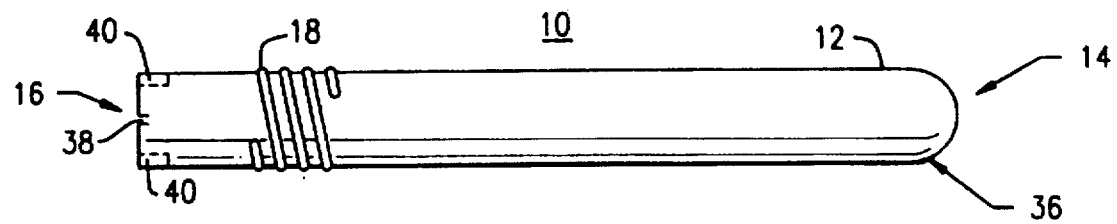
FIG. 1A is an elevational view of an exemplary embodiment of the filling prosthesis of the present invention.

Referring to FIG. 1A, there is shown an exemplary preferred embodiment of the bone core channel filling prosthesis made in accordance with the present invention designated by the numeral 10. The filling prosthesis 10 comprises a machined cylindrical rod-shaped member 12 having a first end 14 and a second end 16. The rod-shaped member 12 has a preferred diameter of approximately 10 mm and a preferred length of approximately 100 mm. One of ordinary skill in the art will recognize, however, that in order to accommodate a broad patient population, the rod-shaped member can also be manufactured in other diameters and length combinations.

Figure 1B:
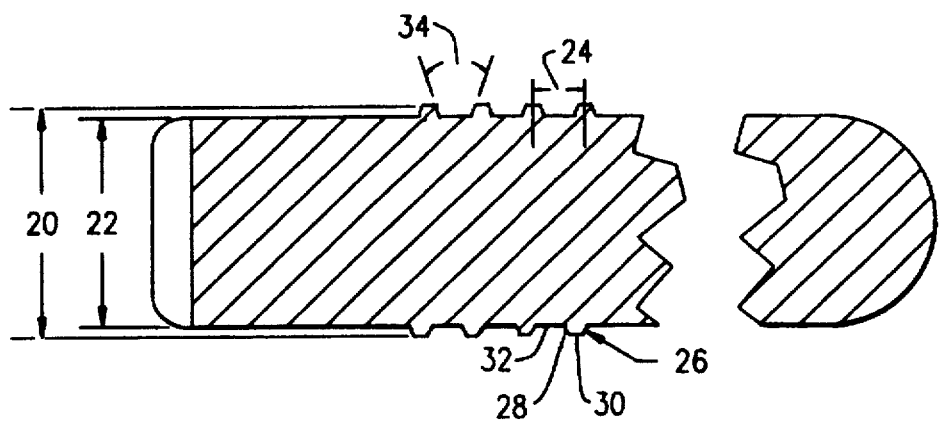
FIG. 1B is a cross-sectional view of the filling prosthesis of FIG. 1A.
Figure 2:
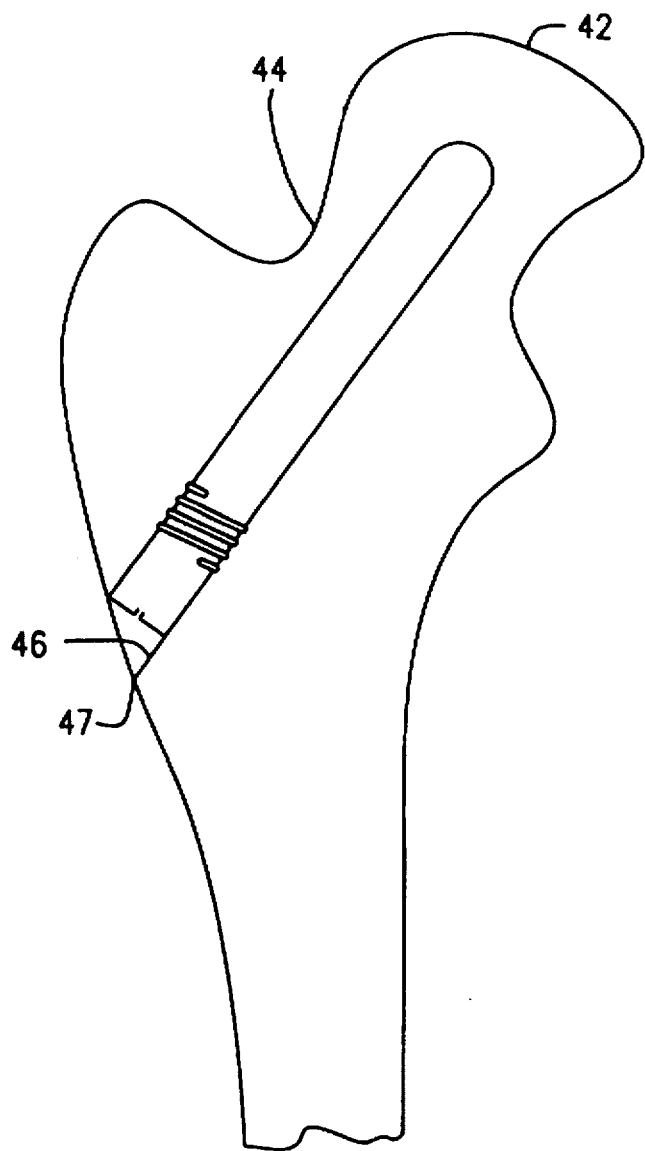
FIG. 2 depicts the filling prosthesis of FIGS. 1A–1C implanted into a cored channel made in the femoral head.

The filling prosthesis 10 includes fixation means for affixing the prosthesis within the core channel. In the preferred embodiment shown, the fixation means comprises a single helical thread 18 having approximately four 360° thread rotations, disposed on the outer surface of the rod-shaped member 12. As shown in FIG. 1B, the thread 18 defines a major diameter 20 of approximately 12 mm and a minor diameter 22 of approximately 10 mm. The pitch 24 of the thread 18 is approximately 3 mm. Each thread rotation includes a substantially flat inclined leading face 26, a substantially flat inclined trailing face 28, a substantially flat crest 30 and a substantially flat root 32. The inclined leading face 26 and the inclined trailing face 28 define an angle 34 of approximately 30.0°. The trailing end of the thread 18 starts approximately 10 mm from the second end 16 of the rod-shaped member 12 and extends therealong approximately 20 mm. The thread 18 of the filling device 10 cuts into the wall of the core channel 46 as shown in FIG. 2, to provide immediate intraoperative stability to the femoral head 42 and neck 44 and to prevent the filling prosthesis 10 from dislodging from the core channel 46.

Figure 1C:
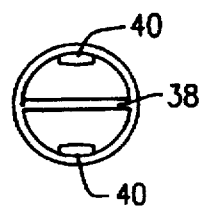
FIG. 1C is a elevational view from the second end of the filling prosthesis shown in FIGS. 1A and 1B.

Referring again to FIG. 1A, the first end 14 of the rodshaped member 12 has a full spherical radius 36 which allows the first end 14 of the rod-shaped member 12 to be easily inserted into the core channel to reside in the femoral head. The second end 16 of the rod-shaped member 12 includes turning means for screwing the filling prosthesis 10 into its final seating position in the core channel of the femoral head. In the preferred embodiment shown, the turning means comprises a slot 38 which extends diametrically along the second end of the rod-shaped member 12 and a pair of opposing recesses 40 as best seen in FIGS. 1A and 1C. The slot 38 and the pair of opposing recesses 40 are adapted to receive a filling prothesis driving tool (not shown).

The filling prosthesis 10 described above, should be made from a highly porous material having a structure of interconnecting pores which accommodates tissue ingrowth, revascularization and deposition of new bone. The material chosen should allow for accurate machining to enable the filling prosthesis to properly fill the cored channel.

The use of a material having a volumetrically large porous structure is important in the present invention because such a structure is complementary to the microstructure of natural cancellous bone and thus, enables the filling prosthesis 10 of the present invention to operate as a matrix for the biological ingrowth of bone. The porous structure of the filling device of the present invention, operates as a conduit from the healthy, vascularized bone into the avascularized bone of the necrotic area. The pores of the filling prosthesis 10 should form a three dimensional network of continuously connected never-ending channels which define a bulk volume porosity of approximately 50–90 percent and preferably greater than 80 percent. Such a network provides optimal permeability and a high surface area which encourages tissue ingrowth, vascularization, and deposition of new bone. The material used in the present invention should also have a high corrosion and crack resistance, and be biocompatible.

In the preferred embodiment of the present invention, the filling prosthesis is made from an open-celled lattice tantalum-carbon composite material available from Implex Corporation, the assignee herein, under the tradename HEDROCEL. HEDROCEL is well known in the art as a composite of reticulated vitreous carbon foam and tantalum metal. The tantalum metal provides the carbon foam with the requisite mechanical properties which the carbon foam does not, by itself, possess. The composite is made by applying tantalum metal to a reticulated vitreous carbon foam construct in a chemical vapor infiltration process (CVI), which is a variation of chemical vapor deposition (CVD). Tantalum has a long history of use as an implant material in bone tissue since it possesses good mechanical a properties, excellent corrosion resistance and demonstrated biocompatibility.

The following method viewed in conduction with FIG. 2, describes how the filling prosthesis of the present invention is used to treat a necrotic region in the femoral head 42. The method comprises removing a core of bone from an anterolateral segment of the femoral head 42 to provide an open channel 46 therein. The first end 14 of the filling prosthesis 10 of the present invention is then inserted into the open channel 46 until the threads 18 contact the external lateral femoral bone 47. Then, a filling prosthesis driving tool (not shown) is used to turn the filling prosthesis into its final position in the bone as depicted in FIG. 2. In hard bone, a tapping instrument can be used in a preparation to receive the threads of the filling prosthesis.

The filling prosthesis of the present invention overcomes the problems associated with the bone grafting techniques described earlier which provide insufficient structural stability to the bone. Further, the filling prosthesis of the present invention possesses the needed biological interface characteristics that are lacking in the prior art solid metal drills and threaded pins.

It should be understood that the embodiment described herein is merely exemplary and that a person skilled in the art may make many variations and modifications to the embodiment utilizing functionally equivalent elements to those described herein. Any and all such variations or modifications as well as others which may become apparent to those skilled in the art, are intended to be included within the scope of the invention as defined by the appended claims.

I we claim:

1. A prosthesis for interfacing with an internal region of a femoral bone, comprising:

porous filling means for filling a cored channel provided in the internal region of a femoral head, said porous filling means comprising a unitarily formed rod-shaped member of reticulated vitreous carbon foam having tantalum deposited thereon, wherein said unitarily formed rod-shaped member has a first end, a second end, and a thread located marginally adjacent to said second end, said thread having a pitch of approximately 3 mm and substantially flat roots and crests whereby said porous filling means provides mechanical stability which preserves the function and the structure of the bone and accommodates an ingrowth of healthy vascularized bone tissue into the internal region of the bone.

2. The prosthesis according to claim 1, wherein the internal region is an avascularized necrotic region of said femoral head and said porous filling means comprises a volumetrically large porous structure of interconnecting pores that operate as conduits which allow the healthy vascularized bone tissue to pass into the avascular necrotic region of the bone.

3. The prosthesis according to claim 1, wherein said porous filling means comprises a bulk volume porosity between approximately 50 and 90 percent.

4. The prosthesis according to claim 1, wherein said first end of said rod-shaped member comprises a spherical-shape.

5. The prosthesis according to claim 1, wherein said second end of said rod-shaped member comprises means for driving said prosthesis into the cored channel of the bone.

6. A core channel filling prosthesis for interfacing with an internal region of a femoral head to substantially prevent the femoral head from collapsing and fracturing, comprising:

a unitarily formed porous rod-shaped member having a first end, second end, and a thread located marginally adjacent to said second end, said thread having a pitch of approximately 3 mm and substantially flat roots and crests, said member for filling a cored channel provided in the internal region of the femoral head, said porous member comprising reticulate vitreous carbon foam having tantalum deposited thereon, said foam forming a volumetrically large structure of interconnecting pores which operate as conduits which allow healthy vascularized bone tissue to pass into the internal region of the femoral head, whereby said prosthesis provides mechanical stability which preserves the function and the structure of the femoral head.

7. The prosthesis according to claim 6, wherein said first end of said porous rod-shaped member comprises a spherical-shape and said second end of said rod-shaped member comprises means for driving said device into the cored channel of the femoral head.

8. The prosthesis according to claim 6, wherein said porous rod-shaped member comprises a bulk volume porosity of between approximately 50–90 percent.

9. The prosthesis according to claim 6, wherein said internal region is an avascularized necrotic region of the bone.

* * * * *